United States Patent
Suga et al.

(10) Patent No.: US 7,202,476 B2
(45) Date of Patent: Apr. 10, 2007

(54) CHARGED-PARTICLE BEAM INSTRUMENT

(75) Inventors: Mitsuo Suga, Saitama-ken (JP); Tomohiro Mihira, Saitama-ken (JP)

(73) Assignee: JEOL Ltd., Tokyo (JP)

( * ) Notice: Subject to any disclaimer, the term of this patent is extended or adjusted under 35 U.S.C. 154(b) by 0 days.

(21) Appl. No.: 11/369,674

(22) Filed: Mar. 7, 2006

(65) Prior Publication Data

US 2006/0219914 A1    Oct. 5, 2006

(30) Foreign Application Priority Data

Mar. 11, 2005    (JP)    ............................. 2005-068781

(51) Int. Cl.
*G21K 7/00*    (2006.01)
*G01N 23/00*    (2006.01)

(52) U.S. Cl. ...................................... 250/310
(58) Field of Classification Search ..................... None
See application file for complete search history.

(56) References Cited

U.S. PATENT DOCUMENTS

| | | | | |
|---|---|---|---|---|
| 4,052,614 A | * | 10/1977 | Fletcher et al. | 250/306 |
| 5,023,453 A | * | 6/1991 | Adachi et al. | 250/309 |
| 5,777,327 A | | 7/1998 | Mizuno | |
| 6,201,240 B1 | * | 3/2001 | Dotan et al. | 250/310 |
| 6,497,194 B1 | * | 12/2002 | Libby et al. | 118/723 F |
| 6,838,668 B2 | * | 1/2005 | Berger et al. | 250/306 |
| 6,888,136 B2 | * | 5/2005 | Geurts et al. | 250/307 |
| 7,067,808 B2 | * | 6/2006 | Kochi et al. | 250/307 |
| 2004/0188610 A1 | * | 9/2004 | Hirose | 250/310 |
| 2006/0219914 A1 | * | 10/2006 | Suga et al. | 250/311 |

FOREIGN PATENT DOCUMENTS

| JP | 6283127 | 10/1994 |
|---|---|---|
| JP | 9017370 | 1/1997 |
| JP | 11162386 | 6/1999 |

* cited by examiner

*Primary Examiner*—David Vanore
(74) *Attorney, Agent, or Firm*—The Webb Law Firm

(57) ABSTRACT

A charged-particle beam instrument is offered which can inspect side and rear surfaces of a sample. Two electron optical microscope columns are mounted in a vacuum chamber. Each of the microscope columns has an electron gun, a condenser lens system, a deflector, and a secondary electron detector. A sample stage assembly on which a sample is placed is mounted in the vacuum chamber. The stage assembly consists of a rotary stage, an X-stage, and a Y-stage. One of the microscope columns is placed in a position where the electron beam from the column can scan at least an upper part of a side surface of the sample. The other microscope column is placed in a position where the beam from the column can scan at least a lower part of the side surface of the sample.

26 Claims, 6 Drawing Sheets

PRIOR ART

CHARGED-PARTICLE BEAM INSTRUMENT

BACKGROUND OF THE INVENTION

1. Field of the Invention

The present invention relates to a charged-particle beam instrument adapted to inspect samples of workpieces, such as semiconductor devices (e.g., ICs and LSIs), treated in semiconductor fabrication processes, especially edge portions of samples.

2. Description of Related Art

In a fabrication process for fabricating semiconductor devices such as ICs and LSIs, each sample is inspected through observation of the substrate (such as a wafer) (hereinafter referred to as the sample) on which semiconductor devices are fabricated.

Such an inspection of samples is performed nondestructively, for example, by electron beam irradiation with a scanning electron microscope (SEM).

FIG. 1 schematically shows a scanning electron microscope performing an inspection of a sample. In the figure, the microscope has an electron optical microscope column 1 mounted to an upper part of the wall of a vacuum chamber 2.

Mounted inside the microscope column 1 are an electron gun 3, a condenser lens system 4 and an objective lens system 5 for focusing the electron beam from the electron gun onto the sample, deflectors 6 for scanning the beam from the gun 3 over the sample, and an axially symmetrical secondary electron detector 7 for detecting secondary electrons emanating from the sample. The deflectors 6 consist of X and Y deflectors.

A sample stage assembly 9 is mounted inside the vacuum chamber 2. An electrostatic chuck 8 is attached to the top surface of the stage assembly 9. A sample 10 is held to the chuck 8. The stage assembly 9 consists of an X stage and a Y stage for movements in the X- and Y-directions, respectively, such that the sample 10 can be moved within a plane perpendicular to the center axis O.

When a scanning signal is sent to the deflectors 6 from a scanning control circuit 12 that operates according to an instruction from a controller 11, the electron beam focused onto the sample 10 scans a desired area on the sample surface in two dimensions. This scanning induces secondary electrons from the sample 10. The secondary electrons are detected by the secondary electron detector 7. The output from the detector 7 is amplified by an amplifier 13, whose output signal is sent to the controller 11. The controller processes the input secondary electron signal and sends the resulting signal to a display device 14, where a secondary electron image of the sample is displayed.

An X-ray detector (not shown in FIG. 1) is mounted above the sample. When a desired area of the sample is irradiated with the electron beam, characteristic X-rays produced from the area are detected by the X-ray detector. The output signal from the detector is sent to the controller 11. The controller performs elemental analysis of the desired area based on the output signal from the detector which indicates the characteristic X-rays.

The human operator inspects the sample based on observation of the secondary electron image of the desired area or on the elemental analysis.

The inspection of the sample as described above is principally performed on sample surfaces. In recent years, however, there is an increasing necessity to inspect side surfaces, their vicinities (edge portions), and rear surfaces of samples, in addition to front surfaces, for the following reason. Silicon wafers which are typical semiconductor substrates have been increased successively in diameter taking account of cost reduction and other factors from 50 mm to 200 mm through 75 mm, 100 mm, 125 mm, and 150 mm. Recently, silicon wafers having a diameter of 300 mm have appeared. However, the thickness has hardly varied although the diameter has been increased. Therefore, if a scratch or cut is present at an edge of a wafer, the wafer itself easily breaks.

In some cases, particles adhere to edges of wafers. In such a case, as the fabrication process proceeds, the particles move and adhere to the mirror-finished surface where a lithographic pattern is formed. Alternatively, during a thermal process, the particles are removed by a thermal treatment and adhere as filmy matter to the mirror-finished surface.

If particles adhere to the rear surface of a wafer, the particles adhere to the wafer support member. As a result, the surface of a wafer supported next may be contaminated.

In any case, there is a danger that the wafer itself becomes defective. Accordingly, it is necessary to inspect whether there is any scratch, cut, or particles at the edges and on the rear surface of the silicon wafer.

First, an edge can be inspected by the following sequence. The stage assembly 9 is tilted, for example, as shown in FIG. 2 to tilt the sample 10 such that the edge is placed opposite to the microscope column 1. A mechanism for tilting a sample is shown, for example, in JP9017370. Alternatively, the microscope column itself may be tilted without tilting the sample. In a further feasible method, the sample is broken and a part 10' including an edge is held to a holder H such that the edge is placed opposite to the microscope column 1 as shown in FIG. 3.

On the other hand, inspection of the rear surface of a sample is enabled by supporting the sample to an electrostatic chuck such that the rear surface is placed opposite to the microscope column.

However, in a method of tilting the sample or microscope column, it is difficult to inspect edge portions close to the rear surface of the sample or the rear surface itself.

Where the sample is broken as described above, the sample is destroyed. Therefore, in-line inspection cannot be achieved.

In the method where the sample is turned upside down and supported on a holder, in-line inspection cannot be performed because the sample surface having a lithographic pattern is damaged.

SUMMARY OF THE INVENTION

It is an object of the invention to provide a novel charged-particle beam instrument.

A charged-particle beam instrument according to one embodiment of the present invention has at least two charged-particle beam microscope columns mounted in a chamber where a sample stage assembly for carrying a sample thereon is mounted. Each of the microscope columns has means for producing a charged-particle beam, means for focusing the beam onto the sample, and deflection means for scanning the beam over the sample. The charged-particle beam instrument further includes detection means for detecting particles produced from the sample by irradiation of the charged-particle beam and display means for displaying an image of at least a part of the sample based on a signal from the detection means. One of the microscope columns is mounted in a position where the charged-particle beam from this column can scan at least an upper portion of a side surface of the sample. The other microscope column is mounted in a position where the beam can scan at least a lower part of the side surface.

A charged-particle beam instrument according to another embodiment of the present invention has at least two charged-particle beam microscope columns mounted in a chamber where a sample stage assembly for carrying a sample thereon is mounted. Each of the microscope columns has means for producing a charged-particle beam, means for focusing the beam onto a sample, and deflection means for scanning the beam over the sample. The charged-particle beam instrument further includes detection means for detecting particles produced from the sample by irradiation of the charged-particle beam and display means for displaying an image of at least a part of the sample based on a signal from the detection means. One of the microscope columns is mounted in a position lying above an extension plane to the midway plane between the front and rear surfaces of the sample. The other microscope column is mounted in a position lying below the extension plane.

In an instrument according to one embodiment of the present invention, at least two charged-particle beam microscope columns are mounted in a chamber where a sample stage assembly for carrying a sample thereon is mounted. Each of the microscope columns has means for producing a charged-particle beam, means for focusing the beam onto the sample, and deflection means for scanning the beam over the sample. One of the microscope columns is mounted in a position where the beam from the microscope column can scan at least an upper part of a side surface of the sample. The other microscope column is mounted in a position where the beam can scan at least a lower part of the side surface. Consequently, an edge portion close to the rear surface of the sample or a part of the rear surface can be easily inspected. Furthermore, in-line inspection is enabled because the sample or any lithographic pattern formed on the sample is not destroyed.

Other objects and features of the invention will appear in the course of the description thereof, which follows.

DESCRIPTION OF THE PREFERRED EMBODIMENTS

The preferred embodiments of the present invention are hereinafter described in detail with reference to the accompanying drawings.

Figure 4:
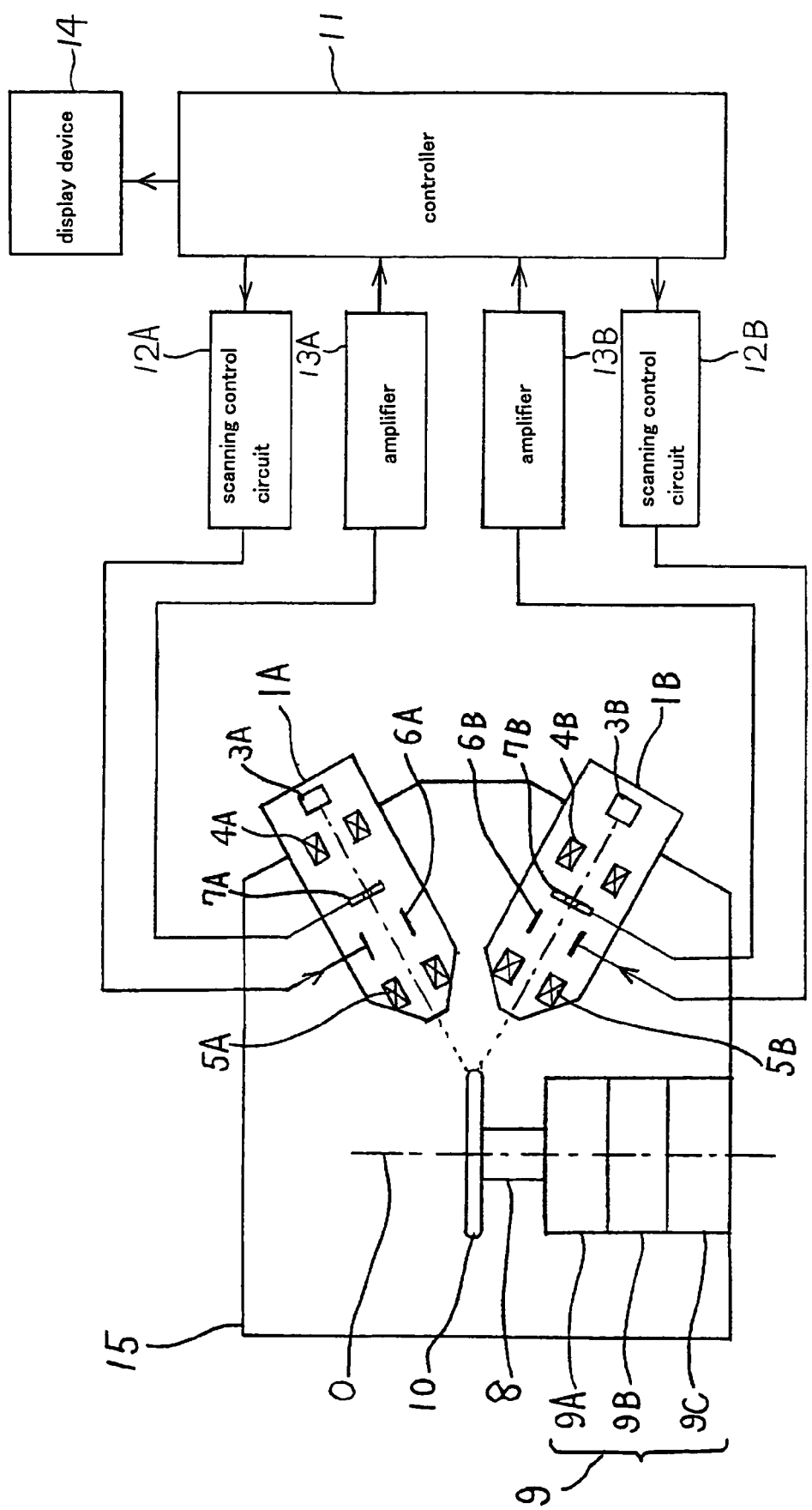
FIG. 4 is a schematic block diagram of an electron-beam inspection system shown as one example of the charged-particle beam instrument of the present invention.

FIG. 4 schematically shows an electron beam inspection system as one example of the charged-particle beam instrument of the present invention. Note that like components are indicated by like reference numerals in both FIGS. 1 and 4.

A sample stage assembly 9 is mounted around the center of the inside of a vacuum chamber 15. An electrostatic chuck 8 is attached to the top surface of the stage assembly 9. The stage assembly 9 consists of a rotary stage 9A capable of rotating a sample 10 along a plane perpendicular to the center axis O, an X-motion stage 9B for motion in the X-direction, and a Y-motion stage 9C for motion in the Y-direction. The sample 10 is held to the chuck 8.

Figure 1:
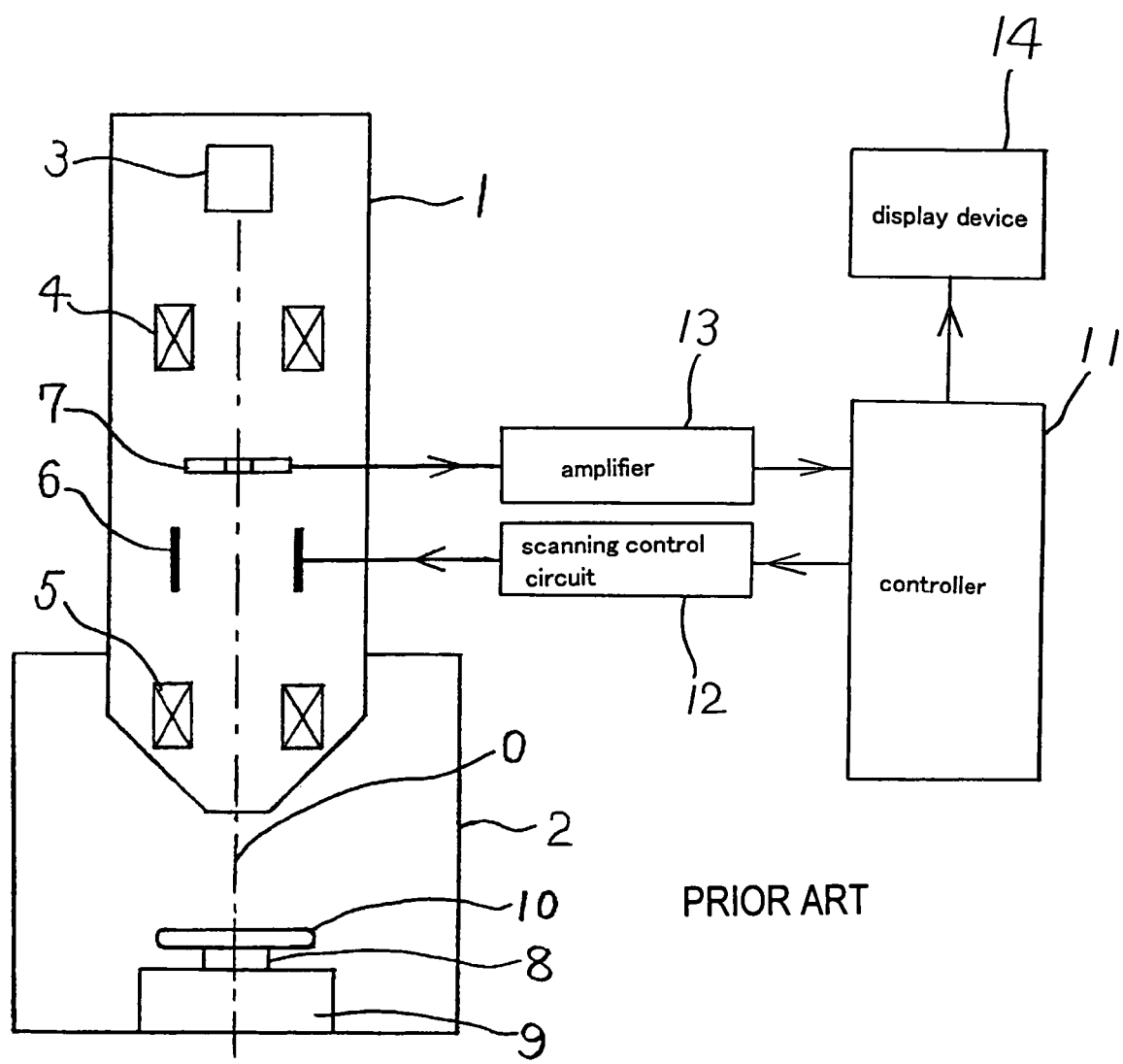
FIG. 1 is a schematic block diagram of a prior art scanning electron microscope for inspecting a sample.
Figure 2:
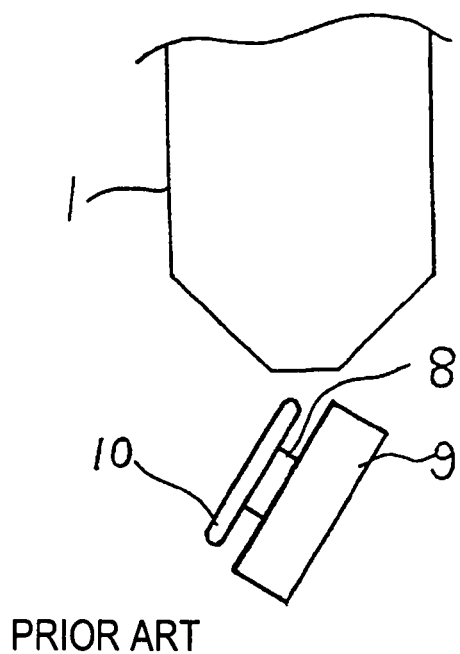
FIG. 2 is a schematic representation illustrating a conventional method for observing a side surface of a sample.
Figure 3:
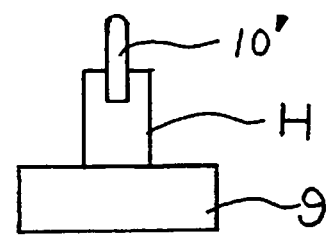
FIG. 3 is a schematic representation illustrating another conventional method for observing a side surface of a sample.

First and second electron optical microscope columns 1A and 1B are similar in structure with the electron optical microscope column 1 shown in FIG. 1. Mounted inside the microscope column 1A are an electron gun 3A, a condenser lens system 4A, an objective lens 5A, a deflector 6A, and an axially symmetrical secondary electron detector 7A. Similarly, an electron gun 3B, a condenser lens system 4B, an objective lens 5B, a deflector 6B, and an axially symmetrical secondary electron detector 7B are mounted inside the microscope column 1B.

The first microscope column 1A is mounted to the side wall of the vacuum chamber 15 above an extension plane of the midway plane between the front and rear surfaces of the sample 10 such that when the sample 10 is in its reference (initial) position, at least the upper half of a side surface of the sample can be scanned, and that when the sample is moved in two dimensions in the X- and Y-directions to shift the sample 10 to the right as viewed in the figure, at least the upper surface of the sample 10 can be scanned.

On the other hand, the second microscope column 1B is mounted to the side wall of the vacuum chamber 15 below the extension plane to the midway plane between the front and rear surfaces of the sample 10 such that when the sample 10 is in its reference position (initial position), at least the lower half of the side surface of the sample can be scanned and that when the sample is moved in two dimensions in the X- and Y-directions to shift the sample 10 to the right as viewed in the figure, at least the lower surface of the sample 10 can be scanned.

Scanning control circuits 12A and 12B supply scan signals to the deflectors 6A and 6B, respectively, according to instructions from the controller 11. Amplifiers 13A and 13B amplify the output signals from the secondary electron detectors 7A and 7B, respectively.

When the sample 10 is placed in its reference position, scanning signals are sent to the deflectors 6A and 6B from the scanning control circuits 12A and 12B, respectively, according to instructions from the controller 11.

The electron beam produced from the electron gun 3A is focused onto an upper part of the side surface of the sample 10 and scanned in two dimensions over the upper part of the side surface. Secondary electrons produced from the sample 10 by the scanning are detected by the secondary electron detector 7A. The output from the detector 7A is amplified by the amplifier 13A and sent to the controller 11. The controller 11 processes the input secondary electron signal by an image processing technique and sends the resulting signal to the display device 14.

Meanwhile, the electron beam emitted from the electron gun 3B is focused onto a lower part of the side surface of the sample 10 and scanned in two dimensions over the lower part of the side surface. Secondary electrons produced from the sample 10 by the scanning are detected by the secondary electron detector 7B. The output from the detector 7B is amplified by the amplifier 13B and sent to the controller 11. The controller processes the input secondary electron signal by an image processing technique and sends the resulting signal to the display device 14.

Figure 5:
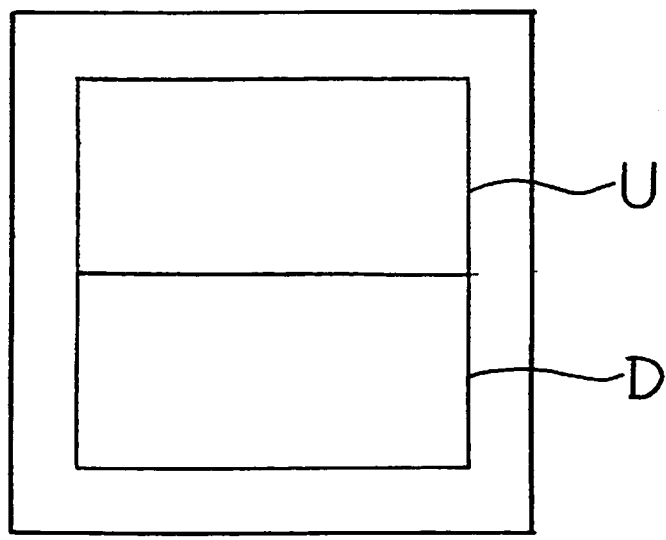
FIG. 5 shows an example of a secondary electron image displayed by an electron beam inspection system according to the present invention.

At this time, as shown in FIG. 5, the controller 11, for example, displays a secondary electron image of the upper half of the side surface of the sample on the upper half U of the display screen of the display device 14 in response to the output signal from the secondary electron detector 7A and displays a secondary electron image of the lower half of the side surface of the sample on the lower half D of the display screen in response to the output signal from the detector 7B.

Then, the rotary stage 9A is rotated stepwise under an instruction from the controller 11. Whenever the stage stops, the upper and lower parts of the side surface are scanned by the electron beams from the microscope columns. Thus, images of the upper and lower parts of the whole side surface are obtained. X-ray detectors (not shown in FIG. 4) are also mounted near the microscope columns, respectively. Characteristic X-rays produced from the upper and lower parts of the side surface of the sample by electron beam irradiation are detected by the X-ray detectors. The resulting detection signals indicative of the X-rays are sent to the controller 11. The controller performs elemental analysis of the parts in response to the input signal indicative of the characteristic X-rays.

In the above embodiment, the secondary electron detectors 7A and 7B are mounted in the microscope columns 1A and 1B, respectively. The detectors may also be placed just beside (e.g., to the left of) the microscope columns as indicated by 7A' and 7B' in FIG. 6. In this configuration, secondary electrons emitted at glancing angles from the sample 10 can be detected and so secondary electron images of various degrees of shade can be obtained. At this time, X-ray detectors 16A and 16B may be placed on the opposite side (to the right of the microscope columns) of the secondary electron detectors 7A' and 7B' from the microscope columns.

Because of this configuration, secondary electron images of the upper and lower parts of the side surface of the sample can be obtained in the same way as in the method illustrated in FIG. 4. At the same time, X-ray analysis of these parts can be performed.

Figure 7A:
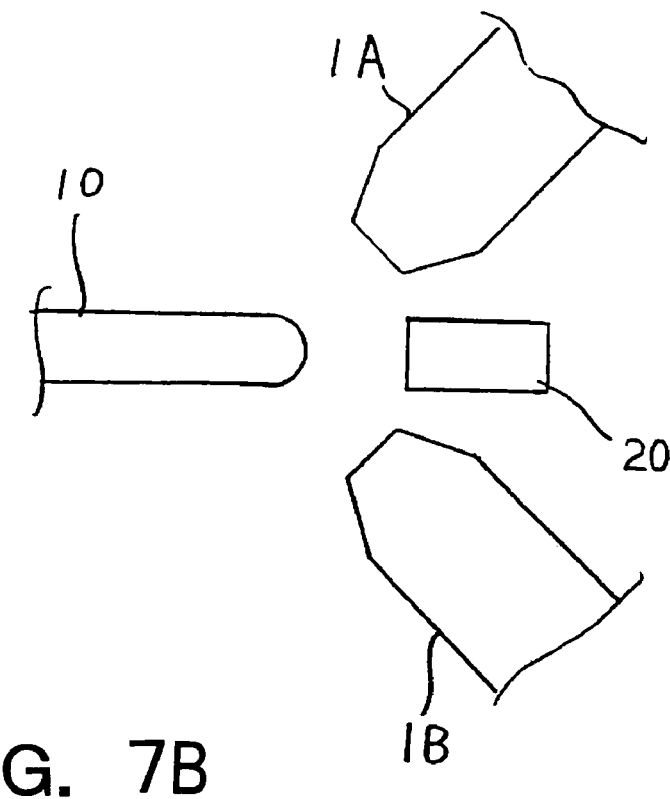
FIGS. 7A and 7B schematically show parts of a further electron beam inspection system according to the present invention.
Figure 7B:
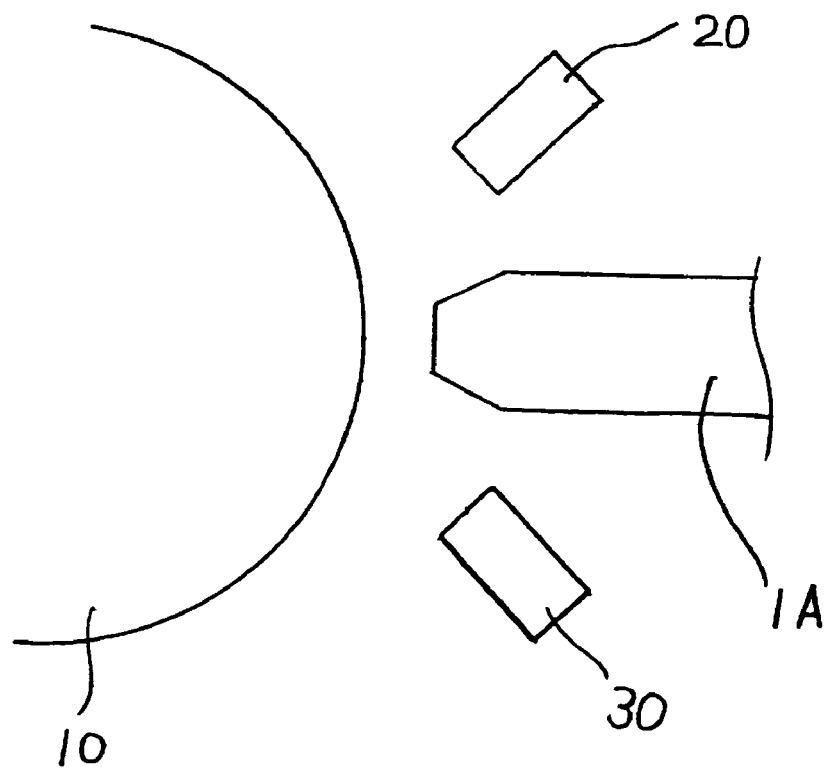

Alternatively, a secondary electron detector 20 and an X-ray detector 30 may be disposed on the opposite sides of the midway position between the two microscope columns 1A and 1B as shown in FIGS. 7A and 7B, unlike the above embodiments where a secondary electron detector and an X-ray detector are mounted in each microscope column. FIG. 7A is a view taken from a direction perpendicular to the center axis O, while FIG. 7B is a view taken from above along the direction of the center axis O. In this configuration, the electron guns and electron optical elements in the electron optical microscope columns are operated in turn to scan the upper and lower halves of the side surface of the sample 10 in turn with the electron beams from the guns. In this way, secondary electron images of the upper and lower halves of the side surface of the sample are obtained. Also, in this case, secondary electrons emitted from the sample 10 at glancing angles can be detected and so secondary electron images having various degrees of shade can be derived.

Figure 6:
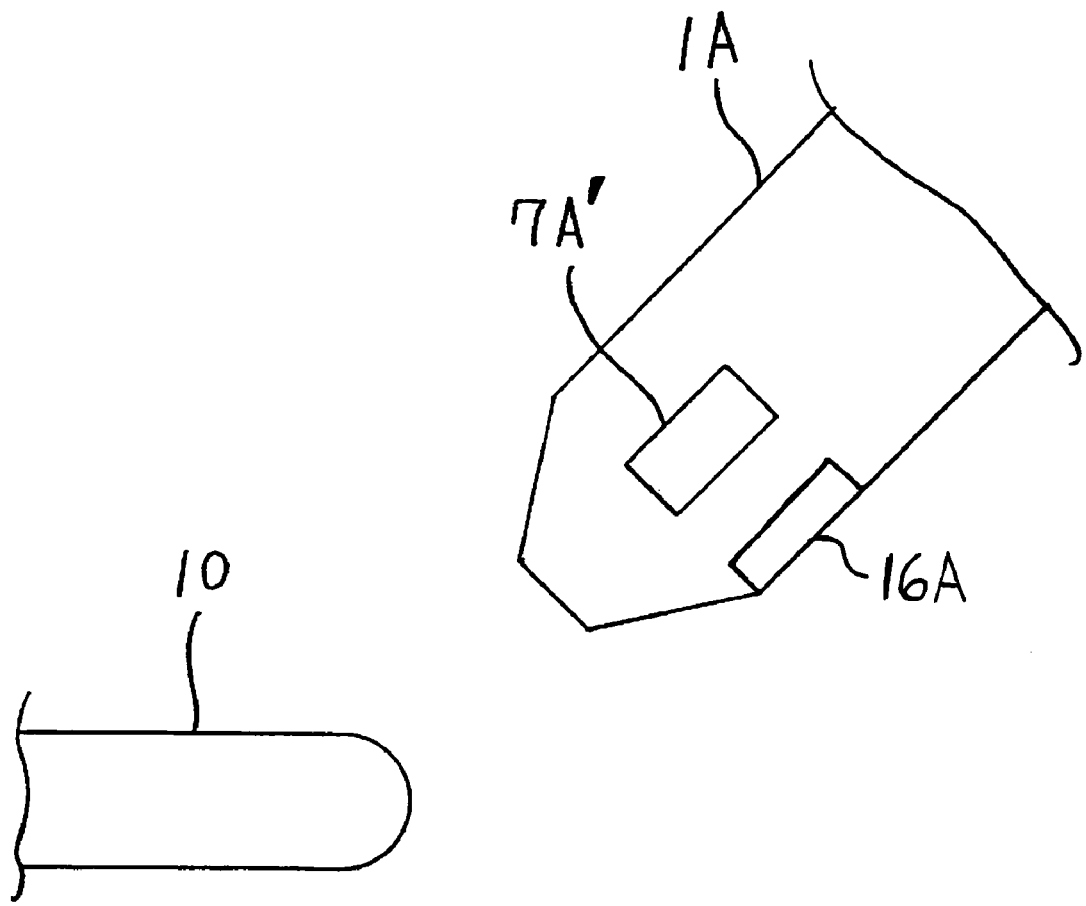
FIG. 6 schematically shows parts of another electron beam inspection system according to the present invention.
Figure 6:
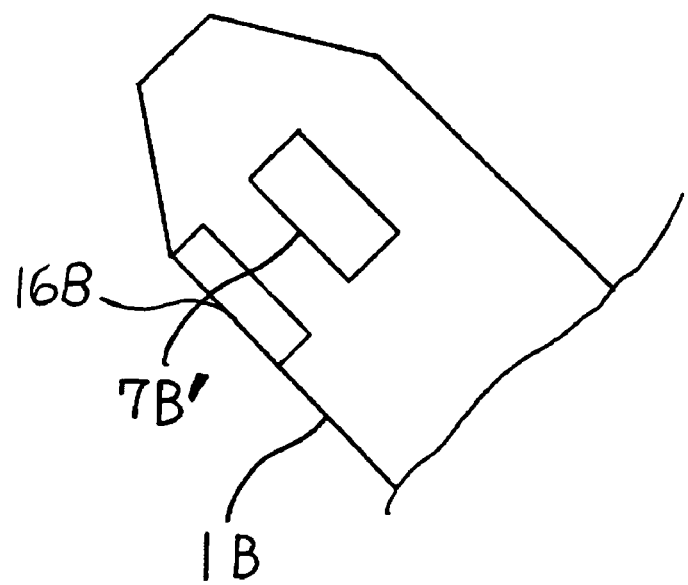
Figure 8:
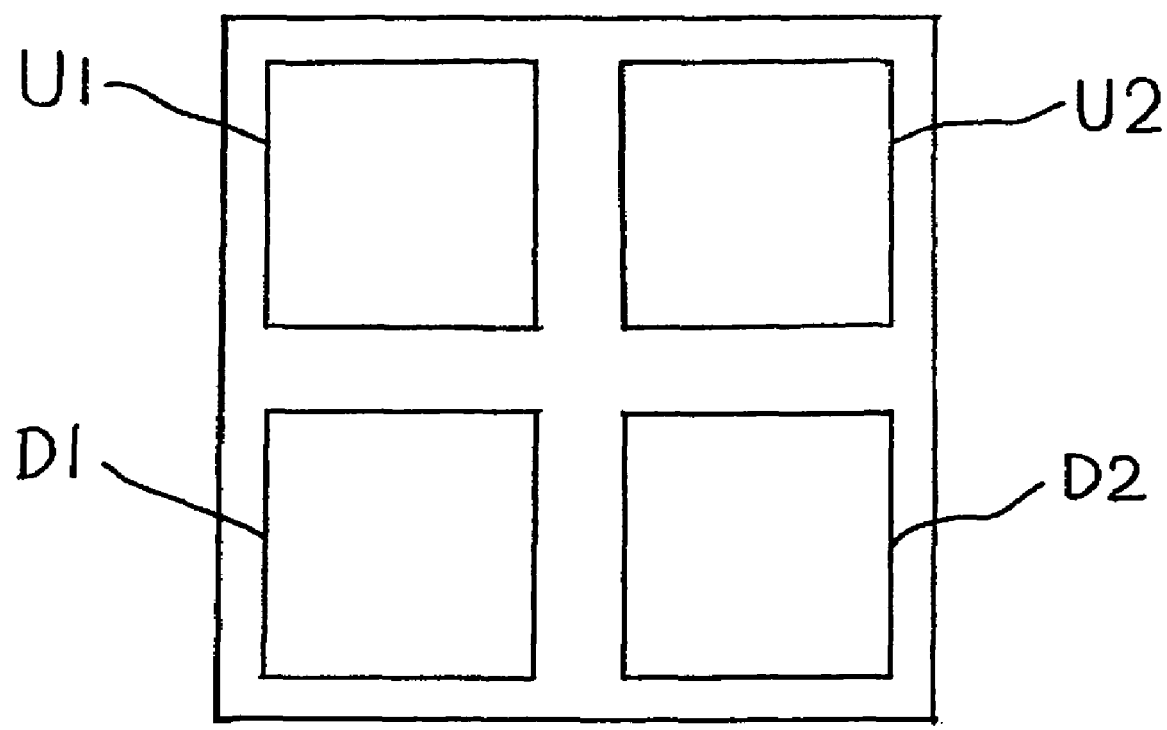
FIG. 8 shows an example of a secondary electron image displayed by an electron beam inspection system according to the present invention.

Alternatively, secondary electron detectors may be mounted inside (as shown in FIG. 4) and outside (as shown in FIG. 6) each microscope column, respectively. Upper and lower parts of the side surface of the sample 10 may be scanned simultaneously by the electron beams produced from the two electron optical microscope columns 1A and 1B, respectively. Secondary electron signals from the detectors may be sent to the controller 11. Secondary electron images created from the output signals from the secondary electron detectors which are placed respectively inside the first electron optical microscope column, inside the second electron optical microscope column, outside the first electron optical microscope column, and outside the second electron optical microscope column. These electron images may be displayed respectively on portions U1, D1, U2, and D2 (FIG. 8) on the display screen of the display device 14. In this case, the secondary electron images of the upper and lower parts of the side surface of the sample 10 displayed respectively on the display parts U2 and D2 have various degrees of shade.

Where the rear or top surface of the sample 10 is inspected, the sample 10 is appropriately moved from its initial reference position toward the microscope column by the X-stage 9B and Y-stage 9C in response to instructions from the controller 11 such that the electron beam from the electron gun 3A of the first electron optical microscope column 1A can scan the upper surface of the sample and that the beam from the gun 3A of the second column 1B can scan the rear surface of the sample.

In the above embodiments, secondary electron images are displayed. Alternatively, electrons reflected from samples may be detected, and backscattered electron images may be displayed.

Furthermore, the sample 10 may be tilted relative to a plane perpendicular to the center axis O using a tilting mechanism as shown in the above-cited JP9017370. Under this condition, the rear surface of the sample may be scanned with the electron beam from the second electron optical microscope column 2B to inspect the rear surface of the sample using a secondary electron signal from the rear surface. In addition, the front surface of the sample may be scanned with the electron beam from the first electron optical microscope column 2A, and the upper surface of the sample may be inspected using a secondary electron signal from the upper surface of the sample.

In the above-described embodiments, an image is obtained based on electron beam scanning. The present invention can also be applied to an instrument that images and displays the scanned portion of the sample based on ion beam scanning.

As used in the following claims, the term "side surface" refers to the surface of a relatively narrow edge of a sample, such as a wafer or thin disc, having roughly parallel surfaces adjacent the side surface.

Having thus described our invention with the detail and particularity required by the Patent Laws, what is desired protected by Letters Patent is set forth in the following claims.

The invention claimed is:

1. A charged-particle beam instrument comprising:
at least two charged-particle beam microscope columns mounted in a chamber where a sample stage assembly for carrying a sample thereon is mounted, each of the microscope columns having means for producing a charged-particle beam, means for focusing the beam onto the sample, and deflection means for scanning the beam over the sample;
detection means for detecting particles produced from the sample by irradiation of the charged-particle beam; and
display means for displaying an image of at least a part of the sample based on a signal from the detection means,
wherein one of the microscope columns is mounted in a position where the charged-particle beam from this column can scan at least an upper portion of a side surface of the sample, while the other microscope column is mounted in a position where the beam can scan at least a lower part of the side surface.

2. A charged-particle beam instrument as set forth in claim 1, wherein said detection means are at least two in kind, and wherein one kind of the detection means is a secondary electron detector, while the other kind of the detection means is an X-ray detector.

3. A charged-particle beam instrument as set forth in claim 1, wherein said detection means are at least two in kind, and wherein one kind of the detection means is a backscattered electron detector, while the other kind of the detection means is an X-ray detector.

4. A charged-particle beam instrument as set forth in claim 1, wherein a charged-particle detection means is mounted in each of said electron optical microscope columns.

5. A charged-particle beam instrument as set forth in claim 1, wherein charged-particle detection means are mounted outside and close to said electron optical microscope columns.

6. A charged-particle beam instrument as set forth in claim 1, wherein charged-particle detection means are mounted respectively inside and outside said electron optical microscope columns in close relationship to the microscope columns.

7. A charged-particle beam instrument as set forth in claim 1, wherein each of said electron optical microscope columns has an intermediate portion in which said detection means for detecting the particles is mounted.

8. A charged-particle beam instrument as set forth in claim 1, wherein a part of the rear surface of the sample is supported on the sample stage assembly.

9. A charged-particle beam instrument as set forth in claim 1, wherein the sample stage assembly is capable of moving the sample in two dimensions along a plane perpendicular to a center axis.

10. A charged-particle beam instrument as set forth in claim 1, wherein the sample stage assembly consists of a rotary stage capable of rotating the sample along a plane perpendicular to a center axis.

11. A charged-particle beam instrument as set forth in claim 1, wherein the sample stage assembly consists of a rotary stage capable of rotating the sample along a plane perpendicular to a center axis and a translational stage capable of moving the sample in two dimensions along the plane perpendicular to the center axis.

12. A charged-particle beam instrument as set forth in claim 1, wherein the sample stage assembly consists of a tilting stage capable of tilting the sample relative to a plane perpendicular to a center axis and a translational stage capable of moving the sample in two dimensions along the plane perpendicular to the center axis.

13. A charged-particle beam instrument as set forth in claim 1, wherein the sample stage assembly consists of a rotary stage capable of rotating the sample along a plane perpendicular to a center axis, a tilting stage capable of tilting the sample relative to a plane perpendicular to the center axis, and a translational stage capable of moving the sample in two dimensions along the plane perpendicular to the center axis.

14. A charged-particle beam instrument comprising:
at least two charged-particle beam microscope columns mounted in a chamber where a sample stage assembly for carrying a sample thereon is mounted, each of the microscope columns having means for producing a charged-particle beam, means for focusing the beam onto the sample, and deflection means for scanning the beam over the sample;
detection means for detecting particles produced from the sample by irradiation of the charged-particle beam; and
display means for displaying an image of at least a part of the sample based on a signal from the detection means, wherein one of the microscope columns is mounted in a position lying above an extension plane to the midway plane between the front and rear surfaces of the sample, while the other microscope column is mounted in a position lying below the extension plane.

15. A charged-particle beam instrument as set forth in claim 14, wherein said detection means are at least two in kind, and wherein one kind of the detection means is a secondary electron detector, while the other kind of the detection means is an X-ray detector.

16. A charged-particle beam instrument as set forth in claim 14, wherein said detection means are at least two in kind, and wherein one kind of the detection means is a backscattered electron detector, while the other kind of the detection means is an X-ray detector.

17. A charged-particle beam instrument as set forth in claim 14, wherein a charged-particle detection means is mounted in each of said electron optical microscope columns.

18. A charged-particle beam instrument as set forth in claim 14, wherein charged-particle detection means are mounted outside and close to said electron optical microscope columns.

19. A charged-particle beam instrument as set forth in claim 14, wherein charged-particle detection means are mounted respectively inside and outside said electron optical microscope columns in close relationship to the microscope columns.

20. A charged-particle beam instrument as set forth in claim 14, wherein each of said electron optical microscope columns has an intermediate portion in which said detection means for detecting the particles is mounted.

21. A charged-particle beam instrument as set forth in claim 14, wherein a part of the rear surface of the sample is supported on the sample stage assembly.

22. A charged-particle beam instrument as set forth in claim 14, wherein the sample stage assembly is capable of moving the sample in two dimensions along a plane perpendicular to a center axis.

23. A charged-particle beam instrument as set forth in claim 14, wherein the sample stage assembly consists of a rotary stage capable of rotating the sample along a plane perpendicular to a center axis.

24. A charged-particle beam instrument as set forth in claim 14, wherein the sample stage assembly consists of a rotary stage capable of rotating the sample along a plane perpendicular to a center axis and a translational stage capable of moving the sample in two dimensions along the plane perpendicular to the center axis.

25. A charged-particle beam instrument as set forth in claim 14, wherein the sample stage assembly consists of a tilting stage capable of tilting the sample relative to a plane perpendicular to a center axis and a translational stage capable of moving the sample in two dimensions along the plane perpendicular to the center axis.

26. A charged-particle beam instrument as set forth in claim 14, wherein the sample stage assembly consists of a rotary stage capable of rotating the sample along a plane perpendicular to a center axis, a tilting stage capable of tilting the sample relative to a plane perpendicular to the center axis, and a translational stage capable of moving the sample in two dimensions along the plane perpendicular to the center axis.

* * * * *